United States Patent
Jusiak et al.

(10) Patent No.: US 6,901,216 B2
(45) Date of Patent: May 31, 2005

(54) INSERTABLE FLUID WARMING CASSETTE UNIT

(75) Inventors: Joel T. Jusiak, Holland, NY (US); David J. Zale, Lancaster, NY (US)

(73) Assignee: Gaymar Industries, Inc., Orchard Park, NY (US)

( * ) Notice: Subject to any disclaimer, the term of this patent is extended or adjusted under 35 U.S.C. 154(b) by 102 days.

(21) Appl. No.: 10/793,547

(22) Filed: Mar. 4, 2004

(65) Prior Publication Data

US 2004/0175165 A1 Sep. 9, 2004

Related U.S. Application Data

(60) Provisional application No. 60/451,731, filed on Mar. 4, 2003.

(51) Int. Cl.[7] .................................................. A61F 7/12
(52) U.S. Cl. ........................ 392/470; 604/113; 165/46
(58) Field of Search ........................ 392/470; 604/93.01, 604/113, 114; 165/46

(56) References Cited

U.S. PATENT DOCUMENTS

| | | | |
|---|---|---|---|
| 3,485,245 A | 12/1969 | Lahr | |
| 4,707,587 A | 11/1987 | Greenblatt | |
| 4,731,072 A | 3/1988 | Aid | |
| 4,737,140 A | 4/1988 | Iroutner et al. | |
| 5,245,693 A | 9/1993 | Ford | |
| 5,875,282 A | 2/1999 | Jordan | |
| 6,464,666 B1 | 10/2002 | Augustine | |
| 2001/0009610 A1 | 7/2001 | Augustine | |
| 2002/0041621 A1 | 4/2002 | Heymann | |
| 2003/0077079 A1 | 4/2003 | Augustine | |
| 2003/0099469 A1 | 5/2003 | Bakke | |

OTHER PUBLICATIONS

European Search Report published on Aug. 4, 2004 (3 pages).

*Primary Examiner*—Thor Campbell
(74) *Attorney, Agent, or Firm*—Roach Brown McCarthy & Gruber, P.C.; Kevin D. McCarthy

(57) ABSTRACT

The present invention is directed to a fluid warming cassette. The cassette has two polymeric films and at least two guide rails. A difference between this fluid warming cassette and those of the prior art is that this fluid warming cassette has a tongue section thereon. This tongue section assists the user insert the cassette into a warming unit's aperture. That aperture is relatively narrow because the heating elements of the warming unit must be sufficiently close to the cassette to alter the temperature of the fluid in the cassette to a desired temperature. In addition, the user can confirm if the cassette is properly inserted into the warming device's aperture by seeing that the tongue portion is sticking out of the other end of the warming device's aperture.

42 Claims, 5 Drawing Sheets

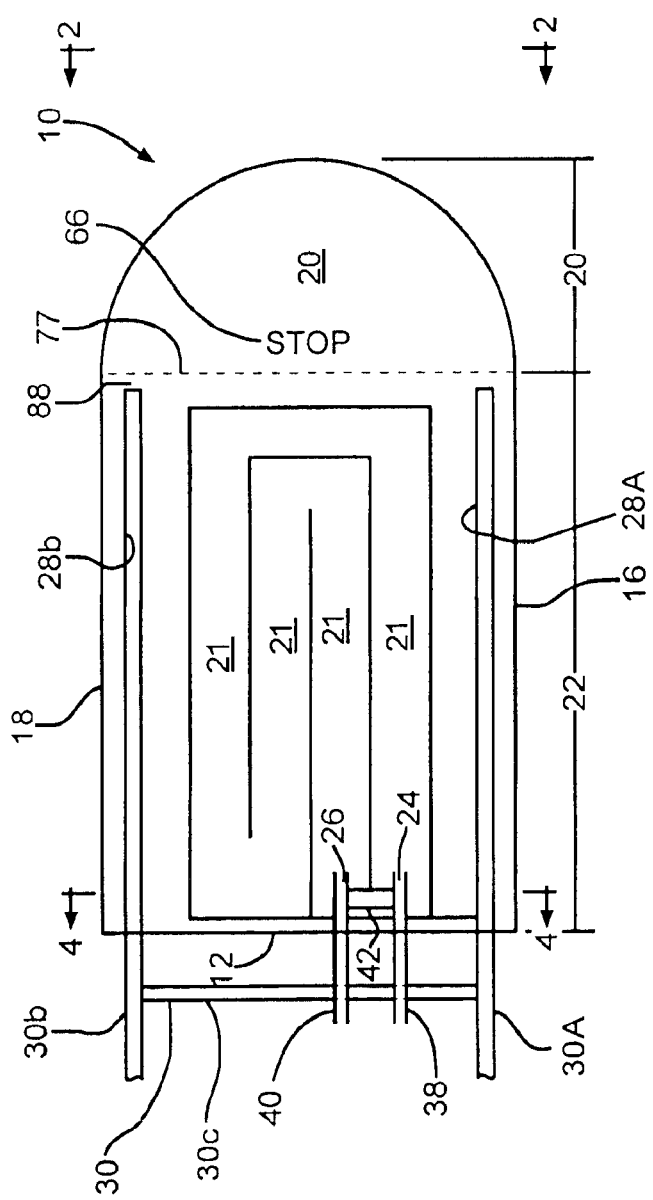
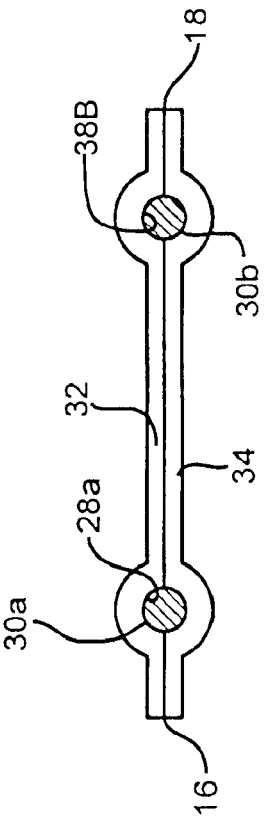

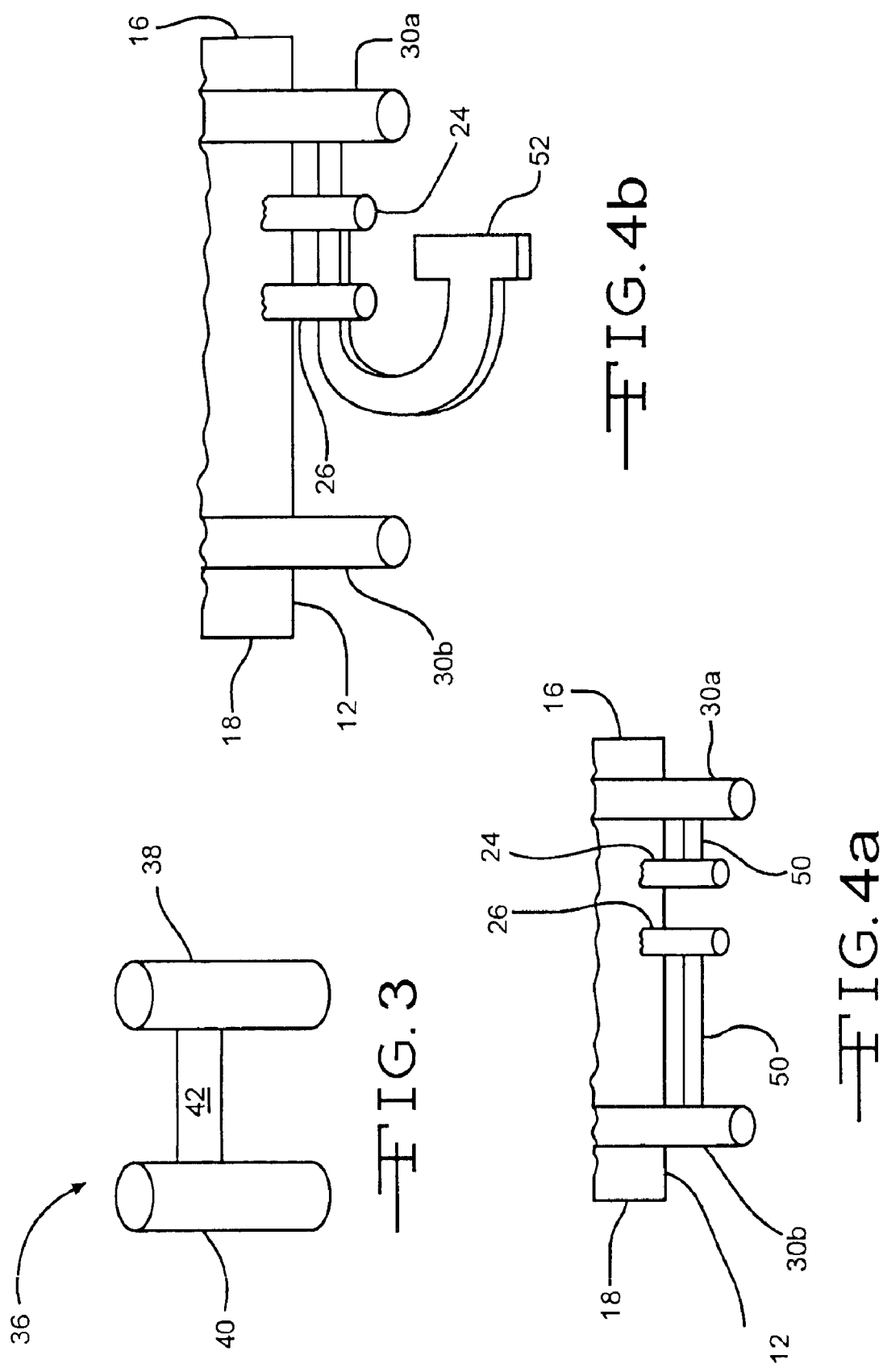

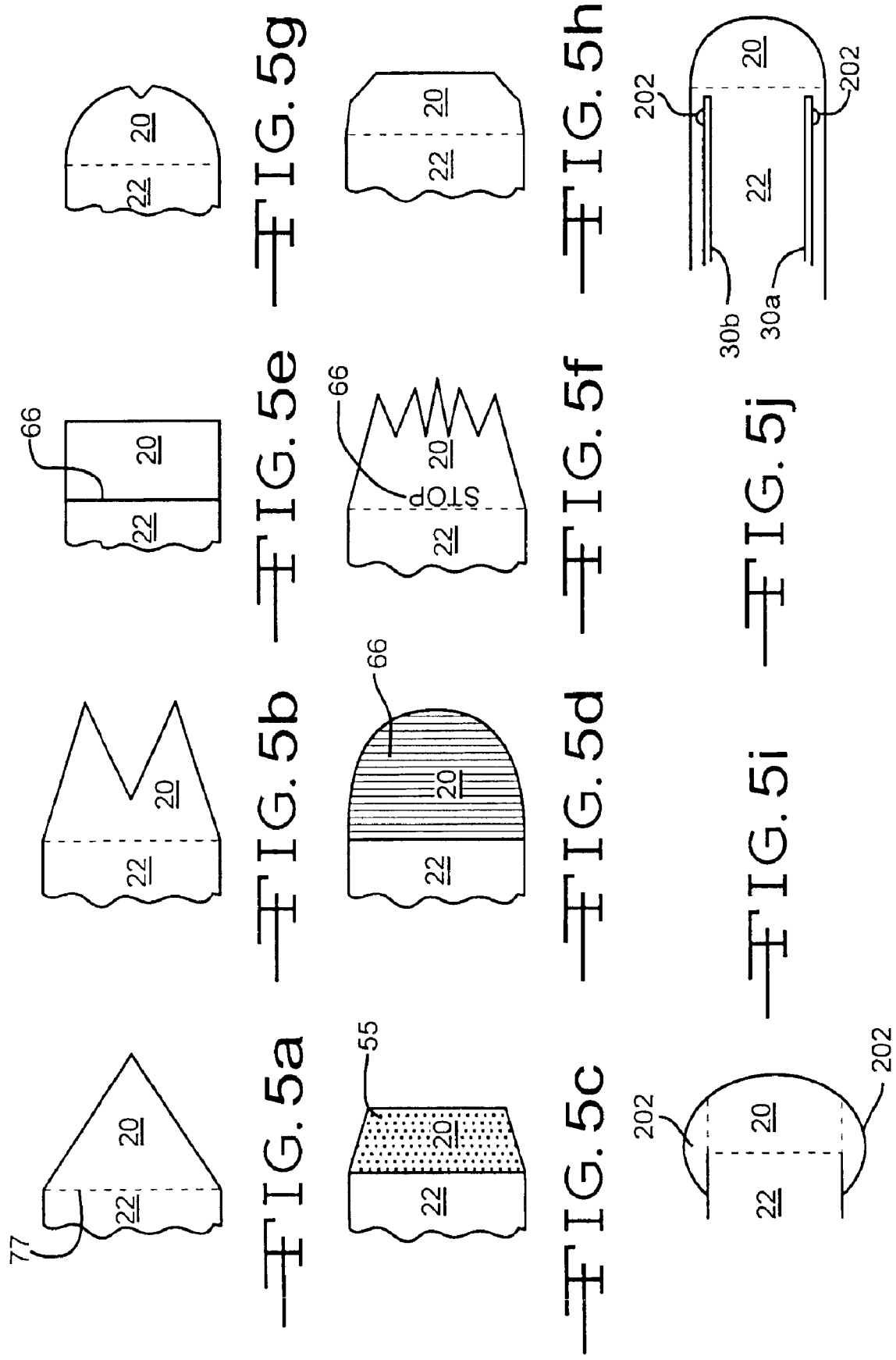

INSERTABLE FLUID WARMING CASSETTE UNIT

CLAIM OF PRIORITY

This application claims priority to U.S. provisional patent application Ser. No. 60/451,731 which was filed on Mar. 4, 2003.

FIELD OF THE INVENTION

The present invention is directed to fluid warming cassettes.

BACKGROUND OF THE INVENTION

There are numerous types of fluid warming cassettes. Some of them are disclosed in U.S. Pat. No. 6,464,666 to Augustine; U.S. Pat. No. 5,875,282 to Jordan et al.; U.S. Pat. No. 4,731,072 to Aid; U.S. Pat. No. 4,707,587 to Greenblatt; and U.S. Pat. No. 3,485,245 to Lahr et al.

Lahr et al. disclose a fluid warming cassette. That fluid cassette has an inlet to allow a fluid enter a counter-flow serpentine fluid path. The counter-flow serpentine fluid path is defined in the fluid warming cassette by joining portions of at least two layers of polymeric film together. The fluid exits the fluid warming cassette through at output. Inlet and outlet conduits transport the fluid to the inlet of and from the outlet of the fluid warming cassette. Neither conduit is integrally connected to the fluid warming cassette. The Lahr et al. design had no guide rails because the fluid warming cassette was inserted into a warming unit having an adjustable aperture to receive the fluid warming cassette. See FIGS. 1–4 of U.S. Pat. No. 3,485,245.

Greenblatt discloses an alternative design of a warming cassette and a warming unit. That warming unit had a non-adjustable aperture to receive a fluid warming cassette. Greenblatt's fluid warming cassette is substantially equivalent to Lahr et al.'s fluid warming cassette except Greenblatt has (1) a plurality of holes along the perimeter of the fluid warming cassette and (2) the inlet and outlet are integrally connected to the cassette but not connected to each other. Greenblatt's fluid warming cassette was then attached to a frame unit that was inserted into the non-adjustable aperture of the warming unit. See FIGS. 7, 8, and 10 of U.S. Pat. No. 4,707,587.

Aid discloses a tapered fluid warming cassette. The warming cassette has a top end, a bottom end, and two sides. The length of the top end is greater than the length of the bottom side, hence the cassette is tapered. At the top end, the cassette has an inlet and an outlet tube integrally connected to a quasi-serpentine fluid path. It is a quasi-serpentine path because the fluid path has "short-cuts" for the fluid to go through. Along each side is a sleeve. The sleeve is designed to receive a stiffener device. The stiffener device is shaped in the letter "U" wherein the extensions of the device go into each sleeve at the top end so the remaining portion of the device acts as a handle for the cassette. In addition, the stiffener device is a guide rail for inserting the cassette into a warming unit's narrower, in relation to the apertures of Lahr et al. and Greenblatt, and non-adjustable aperture. The stiffener device, however, is not an integral part of the cassette and can cause problems with removing and inserting the cassette into and out of the aperture of the warming device. One of those problems can be puncturing the cassette. See FIGS. 2, 7 and 10 of U.S. Pat. No. 4,731,072.

The patent which Jordan et al. are listed as the inventors is assigned to the assignee of this application. In particular, Jordan et al. disclose a fluid warming cassette having a counter-flow serpentine fluid path and two independent inlet and outlet nozzles integrally attached to the cassette. The inlet and outlet nozzles act as a stop mechanism to prevent the cassette from being inserted too far into the aperture of the warming unit. Since Jordan et al.'s cassette is thin; the guide rails are integrally attached to the sides of the cassette. A problem with Jordan et al.'s design is that the cassette is too flimsy and difficult to insert into the warming unit's aperture. See FIG. 3 of U.S. Pat. No. 5,875,282.

Augustine attempts to solve Jordan et al.'s flimsiness issue. Augustine's attempt requires placing a quadrilateral frame structure onto the perimeter of a fluid cassette. That quadrilateral frame must have (1) a stop mechanism positioned at the top end that prevents further insertion of the cassette into the aperture of a warming unit, and (2) guide rails to help assist the cassette into the aperture. In any case, Augustine's frame unit creates further problems. First, it does not solve the insertion problem because the quadrilateral shape is sometimes difficult to align with warming unit's aperature. Second, it requires an expanded aperture of the warming unit to accommodate the quadrilateral frame. By expanding the aperture, the effectiveness of the warming unit is slightly diminished. See FIGS. 1B and 2A of U.S. Pat. No. 6,464,666.

After reviewing these references, we noticed that the bottom end of each fluid warming cassette has two squared or nearly squared corners. That means, the bottom end is essentially parallel to the top end and perpendicular to the other sides. It is our understanding that the bottom end has this shape so the cassette remains within the warming unit.

The present invention has a unique design which solves the flimsiness and insertion problems of Jordan et al. and the other cited references.

SUMMARY OF THE INVENTION

The present invention is directed to a fluid warming cassette. The cassette has two polymeric films and at least two guide rails. A difference between this fluid warming cassette and those of the prior art is that this fluid warming cassette has a tongue section thereon. This tongue section assists the user insert the cassette into a warming unit's aperture and also not alters the spacing of a warming unit's aperture. That aperture is relatively narrow because the heating elements of the warming unit must be sufficiently close to the cassette to effectively alter the temperature of the fluid in the cassette to a desired temperature. In addition, the user can confirm if the cassette is properly inserted into the warming device's aperture by seeing that the tongue portion is sticking out of the other end of the warming device's aperture.

BRIEF DESCRIPTION OF THE DRAWINGS

FIG. 1 is a top view of the present invention.

FIG. 2 is a view of FIG. 1 taken along the lines 2—2.

FIG. 3 is a view of the inlet and outlet tube system.

FIGS. 4a and b are alternative embodiments of FIG. 1 taken along the lines 4—4.

FIGS. 5a to j are alternative embodiments of the tongue section 20, and ear section.

DETAILED DESCRIPTION OF THE INVENTION

Figure 7:
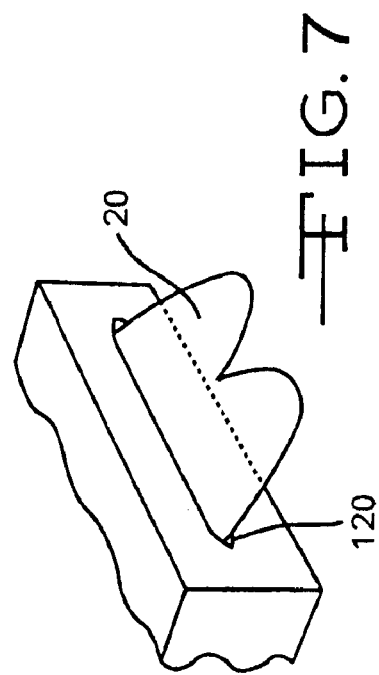
FIG. 7 is a view of FIG. 6 taken along lines 7—7 with the present invention therein.
Figure 6:
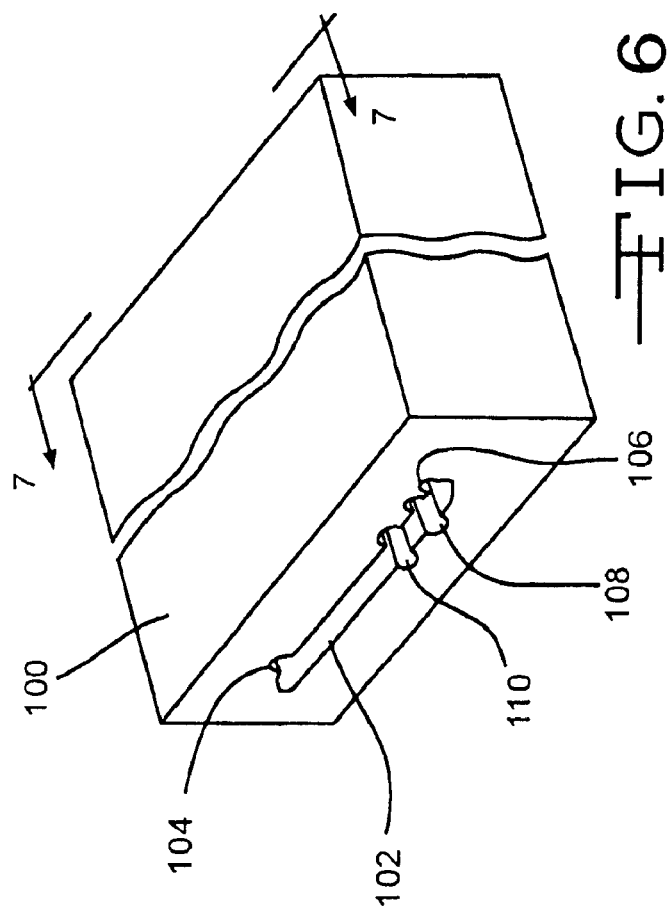
FIG. 6 is a schematic drawing of a conventional warming unit.

The present invention is a fluid warming cassette. Admittedly, this fluid warming cassette is a variation of the cassette disclosed by Jordan et al. because the present invention will be used in a warming unit 100 having an aperture 102, preferably the same size as the one used in and disclosed by Jordan et al.—same assignee as this invention.

The present cassette 10 has a proximal end 12, a distal end 14, a first side 16, a second side 18, a tongue section 20 that is toward the distal end 14, a fluid path 21 within a fluid path section 22 having an inlet 24 and an outlet 26 and positioned between the tongue section 20 and the proximal end 12, and guide rail sections 28a and b. The guide rail section 28a is positioned between the first side 16 and the fluid path section 22 and the second guide rail section 28b is positioned between the second side 18 and the fluid path section 22.

The present cassette 10 is constructed from at least a guide rail system 30 and two relatively thin polymeric films 32, 34. The two relatively thin polymeric films 32, 34 are sealed together in predetermined positions to form at least the guide rail sections 28a and b, and a tortuous pattern for the fluid path section 22. In particular, it is desired that the inlet 24 and outlet 28 of the tortuous pattern be positioned adjacent to each other.

When the inlet 24 and the outlet 26 are adjacent to each other, the applicants can utilize an interconnected inlet/outlet system 36, as illustrated in FIG. 3. The system 36 has an inlet tube 38 that is positioned at the inlet 24, an outlet tube 40 that is positioned at the outlet 26, and an interconnect bar 42 that connects the inlet tube 38 and the outlet tube 40 together. The interconnected inlet/outlet system 36 is attached to the cassette 10 in a superior manner than the individual tube method of Jordan et al. This superior attachment is possible because the system 36 has more planar space in which the films 32, 34 can seal around. Thereby there is less chance that the tubes will be unintentionally released from the seal when the cassette 10 is removed from the warming unit.

The seal between the two films 32, 34 can be accomplished by numerous methods. Many of these methods are conventional to those of ordinary skill in the art. In particular, some of these methods use, and are not limited, radio frequency, heat, ultraviolet, and/or ultrasound to form the desired seals between the films 32, 34.

Prior to the films 32, 34 being sealed, the guide rail system 30, and the inlet tube 38 and the outlet tube 40 (preferably, the system 36), are positioned between the films 32, 34. The films are then sealed so the tubes 38, 40 (and the interconnected inlet/outlet system 36) and the guide rail system 30 are securely positioned to the cassette.

The guide rail system 30 can be a single unit, as illustrated in FIG. 1, or two separate units, as illustrated in FIGS. 4a and b. In either embodiment, there needs to be at least two guide rails 30a and 30b that must be in the respective guide rail section 28a and b. These rails can be the same shape and size. Alternatively, the rails can be different sizes and shapes to ensure the cassette is properly inserted into the warming unit 100. The warming device 100 has guide rail slots 108, 110 that receive the respective rails 30a and b. Those slots 108, 110 can be the same size or different sizes. In any case, the rails 30a and b can be any conventional material, for example, and not limited to, plastic or metal.

In one embodiment, the rails 30a and b are integrally connected together by a support bar 30c. In this embodiment, the support bar 30c acts as a grasping member for the cassette 10. In addition, the support bar 30c can support tubes 38 and 40. With such support, there is a decreased chance the tubes 38 and 40 will be displaced from the cassette 10.

In another embodiment, each rail 30a and b has a support member 50 that supports a respective, preferably adjacent, tube 38 and 40, as illustrated in FIG. 4a.

In another embodiment, at least one rail 30a and b has a support member 52 that supports at least one tube 38 and/or 40, and preferably both tubes, as shown in FIG. 4b.

A version of the tongue section 20 is illustrated in FIG. 1. The tongue section 20 is designed to assist the user of the cassette 10 insert the cassette 10 into the aperture 102. It has been our experience, that the tongue 20 provides stability and ease of insertion of the cassette into the warming unit's aperture. A criterion of the tongue section is that it extends beyond the four corners of the fluid path section 22. The fluid path section must remain within the warming device 100 when the cassette is in the aperture 102. The shape of the tongue can be any shape. For example, the tongue section 20 can be rounded, shaped like a triangle or any other polygon shape, and/or a combination of rounded and polygonal, as illustrated in FIGS. 5a–h. In addition, the tongue section 20 can have various apertures (which can be trademarks and/or designs) within the tongue section, which do not alter the function of the tongue section to stiffen the cassette 10 and assist the user insert the cassette 10 into the aperture 102 of the warming unit 100.

The tongue section 20 can be the same material as the films 32, 34 or a different material. The different material can be other polymeric materials or metal wire. Metal wire has been shown to keep the cassette 10 taut. In one embodiment, the wire is interconnected to the guide rails 30a and b.

In a preferred embodiment, the tongue section 20 is made of a stiffer material than the films 32, 34. If the tongue section is made of a different polymeric material, the tongue section 20 may be sealed to the cassette in a similar manner as the rails 30a and b are to the films 32, 34.

Alternatively, if the tongue 20 material is the same material, the films 32 and 34 can be hardened in the tongue section to make the tongue 20 sturdier than the fluid path section 22. This hardening process can occur by numerous methods. One of those methods is by dipping the tongue section into another polymeric solution that will essentially stiffen the tongue section 20. Other methods include and are not limited to radiating and curing the tongue section 20.

The warming unit 70 has two apertures. The first aperture 102 receives the cassette 10. The other aperture 120 allows the tongue section 20 to stick out of the warming unit 100, when the cassette 10 is positioned within the aperture 102. When the tongue section 20 is fully exposed, the user will know that the cassette 10 is properly positioned within the warming unit 70. In one embodiment, the tongue section 20 and the fluid path section 22 are separated by a perforation 77, or any other equivalent method (for example, scissors, knife, tear, pull, or equivalent thereof) in which to separate the tongue from the fluid path section. Which ever method is used, but preferably the perforated way, allows the user to remove the tongue section once the cassette 10 is properly positioned in the warming unit.

Alternatively, the tongue section 20 has a length that is equal to or greater than the length of the fluid path section 22. That way, when the tongue section 20 is inserted into aperture 102 and exits aperture 120, the user can pull on tongue section 20 to properly position the fluid section 22 in the warming unit 100.

In addition, the tongue section 20, or alternatively the fluid path section 22, can have indicia 66 that indicates when the fluid path section 22 is fully inserted. This indicia can be writing, a line, or a visual indicator, like a change in color for example red, that indicates when the user should stop inserting or pulling the cassette 10 into the aperture 102.

Figure 8A:
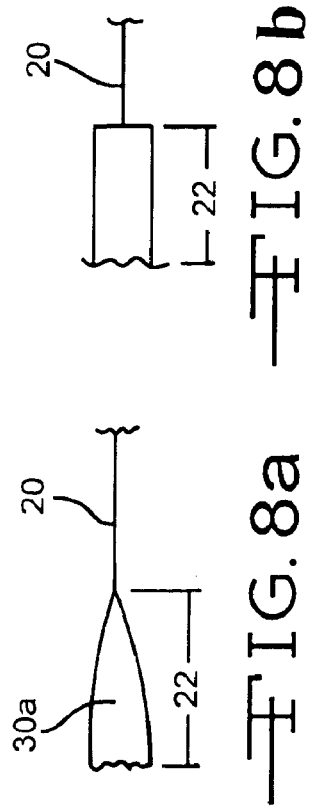
FIGS. 8a–d illustrate alternative embodiments directed to the guide rails and the tongue section of the present invention.
Figure 8B:
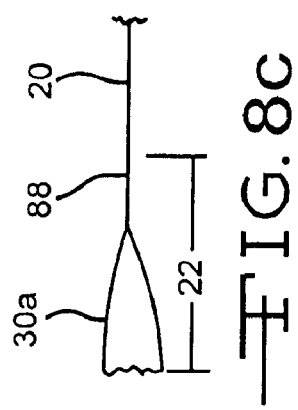
Figure 8C:
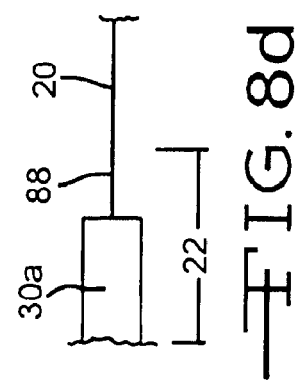
Figure 8D:
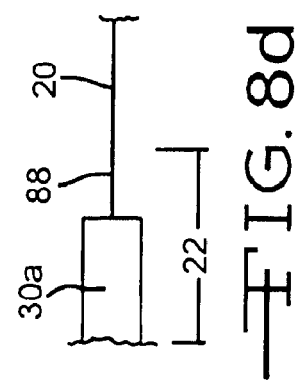

In another embodiment, the guide rails 30a and b at the distal end merge into the tongue section 20, as shown in FIGS. 8a and b. That way, the tongue section 20 acts as a self-guiding apparatus for the rail guides 30a and b. Alternatively, there is a gap 88 between the tongue section 20 and the fluid path section 20, as shown in FIGS. 8c and d.

In another embodiment, the tongue section 20 can have an abrasive 55 thereon. The abrasive 55 can be applied prior to the cassette 10 being inserted into aperture 102 or when the tongue section 20 is already sticking out of aperture 120. In any case, the abrasive material is any conventional material that can clean the heater elements of the warming unit 100. Known abrasive material includes and is not limited to felt, bristle material and pipe cleaner. When the abrasive material 55 is pulled or pushed through the heater elements, the heater elements become clean.

Alternatively, the cassette 10, without a fluid path section 22, can have an abrasive 55 thereon.

Like Jordan et al., the tubes 38 and 40 are the stopping mechanism to prevent over insertion of the cassette 10 into the warming unit, not the guide rail system.

The cassette can also have ear-like projections 202 extending from a portion of the rails 30a,b and/or the tongue section 20. The ears 202 can be made of the same material as the rails 30a,b and/or the tongue section 20. The ears 202 can be positioned on one rails, both rails, or extensions of the tongue section 20. In a preferred embodiment the ears 202 extend from predetermined portions of both rails.

One the predetermined portions can be near the distal end of the rail (near the tongue section 20) and protruding away from the fluid path section. That way, the ears 202 can prevent the cassette from being improperly inserted (for example, backwards) into the warming device. The ears also assist a user in aligning the rails into aperture 102 of the warming device. See FIGS. 5h and i.

Figure 9:
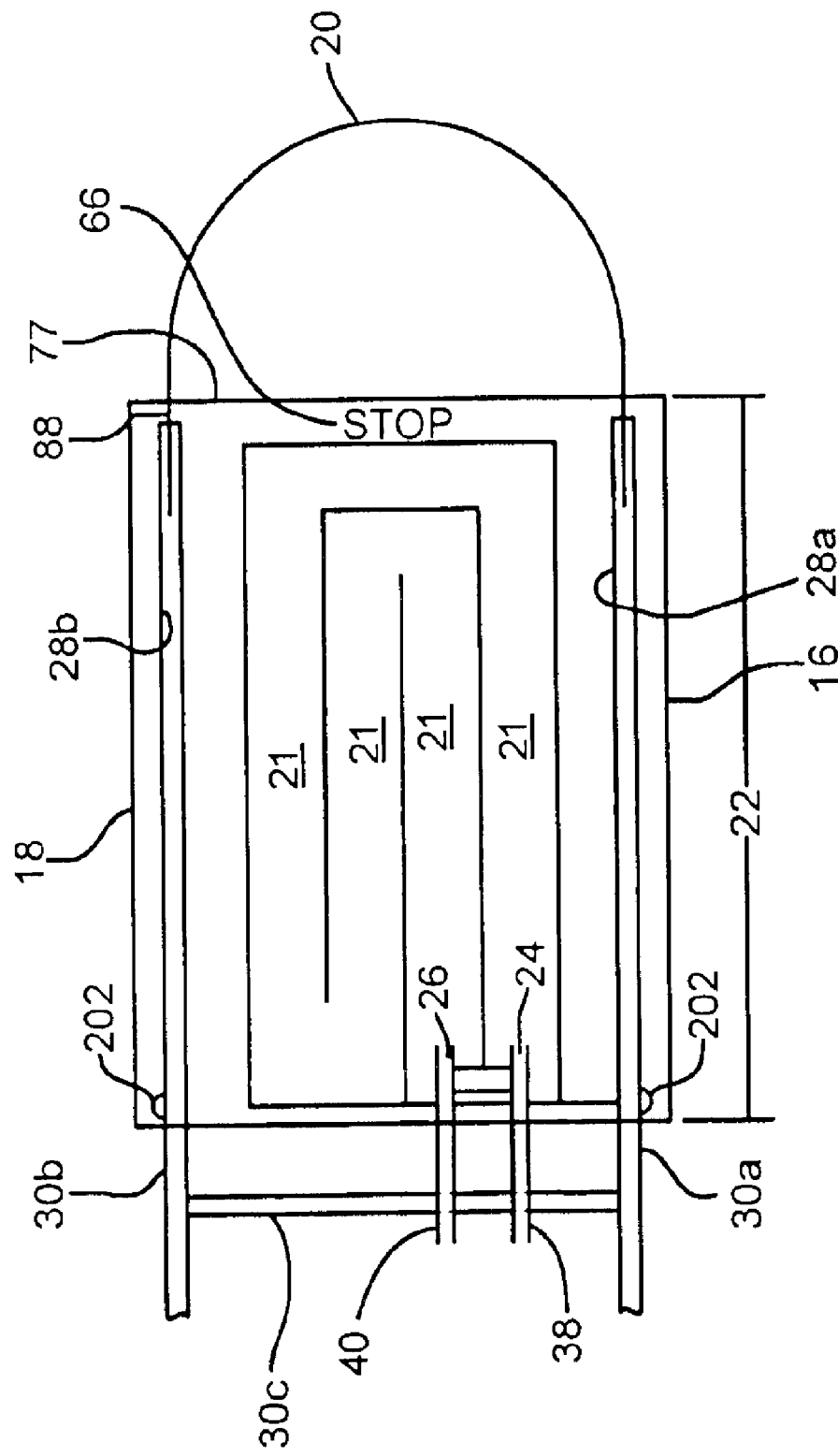
FIG. 9 illustrates an alternative embodiment of FIG. 1.

And in another predetermined position near the distal end of the rails, the ears 202 can act as a hinderance to the continued over-insertion of the cassette into the aperture 102 of the fluid warming device. These ears 202 are not prototypical stop mechanisms, instead they act like a road bump to allow the user to have an indication that the insertion of the cassette is complete. See FIG. 9.

In a preferred embodiment, the films 38, 40 are four thousandth of an inch (0.004") thick polyethylene.

While the preferred embodiment of the invention has been illustrated and described, it will be clear that the invention is not so limited. Numerous modifications, changes, variations, substitutions and equivalents will occur to those skilled in the art without departing from the spirit and scope of the present invention as defined by the appended claims.

We claim:

1. A fluid warming cassette comprising:
    a first polymeric film and a second polymeric film sealed together in predetermined locations to form a tortuous fluid path within a fluid path section of the cassette, the fluid path section is defined by a proximal end of the cassette, a tongue section which extends toward a distal end of the cassette, a first guide rail section and a second guide rail section of the cassette;
    an inlet tube and an outlet tube for fluid to enter and exit the tortuous fluid path, the inlet and the outlet are positioned at the proximal end;
    a first guide rail extending from the proximal end to a distal end of the cassette and positioned in the first guide rail section;
    a second guide rail extending from the proximal end to the distal end and positioned in the second guide rail section;
    the tongue section extends beyond the fluid path section toward the distal end, the tongue section assists a user insert the cassette into a warmer unit's aperture.

2. The cassette of claim 1 wherein the first and second polymeric films are the same material.

3. The cassette of claim 2 wherein the tongue section is a different material than the first and second polymeric films.

4. The cassette of claim 2 wherein the tongue section is the same material as the first and second polymeric films.

5. The cassette of claim 4 wherein the tongue section is stiffer than the first and second polymeric films.

6. The cassette of claim 1 wherein the first and second polymeric films are different materials.

7. The cassette of claim 6 wherein the tongue section is a different material than the first and second polymeric films.

8. The cassette of claim 6 wherein the tongue section is the same material as the first polymeric film.

9. The cassette of claim 1 wherein the inlet tube and the outlet tube are interconnected together.

10. The cassette of claim 1 wherein the first and second rail guides are interconnected together by a support bar.

11. The cassette of claim 10 wherein the support bar supports the inlet tube, the outlet tube or both the inlet tube and outlet tube.

12. The cassette of claim 1 wherein the first or the second rail guide has a support member that supports the inlet tube, the outlet tube or both the inlet tube and outlet tube.

13. The cassette of claim 1 wherein the first and second rail guides have different sizes and/or shapes.

14. The cassette of claim 1 wherein the tongue section and the fluid path section can be separated along a perforation.

15. The cassette of claim 1 wherein the tongue section has an abrasive material thereon.

16. The cassette of claim 1 wherein the tongue section is made of metal.

17. The cassette of claim 16 wherein the metal is metal wire.

18. The cassette of claim 1 wherein there is a gap between the distal portion of at least one guide rail and the tongue section.

19. The cassette of claim 1 wherein the fluid path section or the tongue section has an indicia that informs the user that the cassette is properly positioned within the warming unit.

20. The cassette of claim 1 wherein at least one guide rail merges into the tongue section.

21. A method of inserting a fluid warming cassette into an aperture of a warming unit comprising:
    inserting a cassette having
        a first polymeric film and a second polymeric film sealed together in predetermined locations to form a tortuous fluid path within a fluid path section of the cassette, the fluid path section is defined by a proximal end of the cassette, a tongue section which extends toward a distal end of the cassette, a first guide rail section and a second guide rail section of the cassette;

an inlet tube and an outlet tube for fluid to enter and exit the tortuous fluid path, the inlet and the outlet are positioned at the proximal end;

a first guide rail extending from the proximal end to a distal end of the cassette and positioned in the first guide rail section;

a second guide rail extending from the proximal end to the distal end and positioned in the second guide rail section;

the tongue section extends beyond the fluid path section toward the distal end, into a first side of a warmer unit's aperture; and confirming the cassette is properly inserted in the warmer unit by confirming the tongue section extends through a second side of a warmer unit's aperture.

22. The method of claim 21 wherein the first and second polymeric films are the same material.

23. The method of claim 22 wherein the tongue section is a different material than the first and second polymeric films.

24. The method of claim 22 wherein the tongue section is the same material as the first and second polymeric films.

25. The method of claim 24 wherein the tongue section is stiffer than the first and second polymeric films.

26. The method of claim 21 wherein the first and second polymeric films are different materials.

27. The method of claim 26 wherein the tongue section is a different material than the first and second polymeric films.

28. The method of claim 26 wherein the tongue section is the same material as the first polymeric film.

29. The method of claim 21 wherein the inlet tube and the outlet tube are interconnected together.

30. The method of claim 21 wherein the first and second rail guides are interconnected together by a support bar.

31. The method of claim 30 wherein the support bar supports the inlet tube, the outlet tube or both the inlet tube and outlet tube.

32. The method of claim 21 wherein the first or the second rail guide has a support member that supports the inlet tube, the outlet tube or both the inlet tube and outlet tube.

33. The method of claim 21 wherein the first and second rail guides have different sizes and/or shapes.

34. The method of claim 21 wherein the tongue section and the fluid path section can be separated along a perforation.

35. The method of claim 21 wherein the tongue section has an abrasive material thereon.

36. The method of claim 21 wherein the tongue section is made of metal.

37. The method of claim 36 wherein the metal is metal wire.

38. The method of claim 21 wherein there is a gap between the distal portion of at least one guide rail and the tongue section.

39. The method of claim 21 wherein the fluid path section or the tongue section has an indicia that informs the user that the cassette is properly positioned within the warming unit.

40. The method of claim 21 wherein at least one guide rail merges into the tongue section.

41. The method of claim 21 wherein the cassette has at least one ear-like projection extending from at least one guide rail or the tongue section.

42. The cassette of claim 1 wherein the cassette has at least one ear-like projection extending from at least one guide rail or the tongue section.

* * * * *